(12) United States Patent
Murphy et al.

(10) Patent No.: US 6,468,513 B1
(45) Date of Patent: Oct. 22, 2002

(54) LOW RESIDUE LIQUID ANTIPERSPIRANT COMPOSITION

(75) Inventors: C. Shawn Murphy, Cincinnati, OH (US); Kristin Ann Boyle, Corona del Mar, CA (US)

(73) Assignee: The Andrew Jergens Company, Cincinnati, OH (US)

( * ) Notice: Subject to any disclaimer, the term of this patent is extended or adjusted under 35 U.S.C. 154(b) by 0 days.

(21) Appl. No.: 10/078,838

(22) Filed: Feb. 19, 2002

(51) Int. Cl.$^7$ .............................. A61K 7/32; A61K 7/34; A61K 7/36; A61K 7/38; A61K 7/00
(52) U.S. Cl. .............................. 424/65; 424/66; 424/67; 424/68; 424/400; 424/401
(58) Field of Search .......................... 424/65, 400, 401

(56) References Cited

U.S. PATENT DOCUMENTS

| | | |
|---|---|---|
| 4,563,346 A | 1/1986 | Deckner |
| 4,784,844 A | 11/1988 | Thimineur et al. |
| 5,626,856 A | 5/1997 | Berndt |
| 5,654,362 A | 8/1997 | Schulz, Jr. et al. |
| 5,880,210 A | 3/1999 | Schulz, Jr. et al. |
| 5,942,215 A | 8/1999 | Edwards et al. |

FOREIGN PATENT DOCUMENTS

| | | |
|---|---|---|
| EP | 0 400 546 B1 | 12/1993 |
| EP | 0 251 679 A1 | 1/1998 |
| WO | WO 97/15270 | 5/1997 |
| WO | WO 98/09612 | 3/1998 |
| WO | WO 99/26597 | 6/1999 |
| WO | WO 99/51192 | 10/1999 |
| WO | WO 00/69402 | 11/2000 |

*Primary Examiner*—Shelley A. Dodson
(74) *Attorney, Agent, or Firm*—Frost Brown Todd LLC

(57) ABSTRACT

Liquid antiperspirant compositions, such as those used in roll-on formulations, are disclosed. These compositions do not leave a significant white residue on the skin of the user and exhibit good skin feel when applied. The antiperspirant liquid compositions of the present invention comprise from about 10% to about 70% of an antiperspirant active; from about 20% to about 80% of a volatile solvent; from about 0.5% to about 2% of a high molecular weight silicone material (such as a silicone gum, dimethicone copolyol, or a crosslinked silicone polymer); from about 0.5% to about 5% of a polyethylene wax, and from about 1% to about 8% of hydrophobic organic esters (such as cetearyl ethylhexanoate).

15 Claims, No Drawings

LOW RESIDUE LIQUID ANTIPERSPIRANT COMPOSITION

TECHNICAL FIELD

The present invention relates to personal care antiperspirant compositions and particularly relates to liquid antiperspirant compositions which are applied topically to the skin (i.e., roll-on compositions).

BACKGROUND OF THE INVENTION

Deodorant and antiperspirant compositions are well-accepted and popular modes of personal care and personal hygiene. As a supplement to the periodic bathing of the body, these compositions counteract odors and prevent perspiration which can occur on the body between times that the body is washed. Deodorant and antiperspirant compositions are generally applied topically to the skin, for example in the underarm area, and there are a wide variety of compositions which can be used to do this. For example, solid sticks, liquid roll-ons, cream compositions, gel compositions, and aerosol sprays are but some of the forms which deodorant and antiperspirant compositions can take. The feel of a particular composition as it is applied to the skin (i.e., its perceived wetness and tackiness) is very important to the user and is frequently a determining factor in whether that composition will be repurchased in the future.

The primary consumer benefit of an antiperspirant or deodorant product is clearly its antiperspirant or deodorant efficacy. However, in addition to such primary efficacy, the fact that a composition does not leave a white residue on the skin or clothing and also provides good skin feel are two very important cosmetic benefits of an antiperspirant or deodorant product. In the past, delivering a nonwhitening product has been accomplished by means of mechanical processing of the product or use of butylene glycol in the product. Mechanical processing is limited in that high shear mixing can only achieve a certain level of nonwhitening on the skin. While butylene glycol is effective as a nonwhitening agent, its use in a liquid composition can result in an undesirable sticky and tacky feel when the composition is applied to the skin.

It clearly would be very useful to have an efficacious antiperspirant composition, formulated as a liquid roll-on, which does not leave a white residue and also has good skin feel properties when applied topically. This result is obtained, as described herein, by formulating a liquid antiperspirant composition which includes an antiperspirant active, a volatile carrier, such as a cyclic siloxane, a high molecular weight silicone material, and a formulation aid selected from polyethylene, hydrophobic organic esters, and mixtures of those materials.

PCT Patent Application WO 99/51192, published Oct. 14, 1999, describes a gel form antiperspirant composition which is said to reduce white residue on skin and improve skin feel, while reducing syneresis of the composition on storage. The composition comprises a silicone gel containing a crosslinked polyorganosiloxane elastomer and at least one nonionic surfactant having an HLB of from 8 to 16, together with an antiperspirant active. It is thought that the composition may be formulated as a solid, semi-solid, cream or liquid having a viscosity of at least about 1000 cps; roll-on compositions are specifically disclosed. For example, the application discloses a roll-on antiperspirant composition which includes a silicone cross-polymer, a volatile silicone, an antiperspirant active, a nonionic surfactant, emollients, a thickener, and fragrance components.

European Patent Application EP 0 251 679, published Jan. 7, 1988, describes a solid stick composition for delivering skin treating or cosmetic materials to the skin. The stick comprises a stable alcohol-silicone mixture gelled by a sodium salt of a higher fatty acid (such as sodium stearate). The composition includes a polydiorganosiloxane-polyoxyalkyene copolymer and a volatile silicone. The entire basis of this invention is the formulation of a solid stick which is compatible with an antiperspirant active; the composition is not a liquid roll-on.

PCT Patent Application WO 00/96402, published Nov. 23, 2000 discloses low residue antiperspirant compositions which comprise cyclohexasiloxane as the volatile siloxane component, and which are substantially free of cyclotetrasiloxane. Examples 1–7 of the application describe aqueous emulsion compositions which contain dimethicone copolyol. Examples 13–15 of the application describe antiperspirant roll-on compositions which include polyethylene powder.

European Patent Application EP 0 400 546, published Dec. 8, 1993, describes a topical composition for delivering an active material (which may be an antiperspirant active) to the skin. The composition may be formulated as a liquid roll-on. The composition comprises an antiperspirant active, a volatile carrier (such as cyclomethicone), finely divided silica, a wax, and an ester including at least 10 carbon atoms (such as dioctyl adipate).

PCT Patent Application WO 99/26597, published Jun. 3, 1999, describes antiperspirant compositions which include borage seed oil to provide a skin anti-irritancy benefit. The application teaches the inclusion of what are said to be conventional ingredients in antiperspirant formulations: volatile carriers (such as cyclomethicone), and nonvolatile emollients (such as fatty alcohol esters, including cetyl palmitate, butyl myristate, and glyceryl stearate).

PCT Patent Application WO 97/15270, published May 1, 1997, describes antiperspirant formulations, in the form of a stick, roll-on or cream, which include bicarbonate crystallites and boron oxide particulates. The boron oxide material is said to neutralize irritant impurities which may be present in the bicarbonate component. The application discloses a roll-on composition which includes an antiperspirant active, a volatile oil (for example, cyclomethicone), and a liquid emollient (such as 2-ethylhexyl palmitate).

PCT Patent Application WO 98/09612, published Mar. 12, 1998, describes solid antiperspirant compositions (which do not include liquid roll-on compositions) containing hexanediol-behenyl beeswax as a gelling agent. The example compositions in the application include cyclomethicone, dimethicone copolyol and polyethylene.

U.S. Pat. No. 5,942,215, Edwards et al., issued Aug. 24, 1999, describes an antiperspirant stick composition (not a liquid roll-on) which includes an antiperspirant active, a volatile silicone (e.g., cyclomethicone), a crosslinked silicone elastomer, and a structurant. The compositions can also include polyethylene as an optional component.

U.S. Pat. No. 5,626,856, Berndt, issued May 6, 1997, describes a topical delivery system for cosmetics and pharmaceuticals comprising a volatile cyclosiloxane, an oil or glyceride ester, and a particulate carbohydrate. The compositions are taught to be useful for antiperspirant products. Example 2 is a liquid antiperspirant composition which includes cyclomethicone, starch, white petrolatum, and an antiperspirant active.

U.S. Pat. No. 5,654,362, Schulz, Jr., et al., issued Aug. 5, 1997, covers Dow 9040 silicone elastomer. Example 3 discloses the use of the silicone elastomer in an antiperspirant formulation; the exemplified composition is said to be highly spreadable, with a dry skin feel and low residue on the skin. This composition includes an antiperspirant active, a silicone powder, and octyl palmitate. See also related U.S. Pat. No. 5,880,210.

SUMMARY OF THE INVENTION

The present invention relates to liquid antiperspirant compositions which comprise:
 (a) from about 10% to about 70% of an antiperspirant active material;
 (b) from about 20% to about 80% of a volatile carrier, such as a volatile siloxane, for example, cyclomethicone;
 (c) from about 0.5% to about 5% of a high molecular weight silicone material, for example, a silicone gum, dimethicone copolyol, or a crosslinked silicone polymer;
 (d) from about 0.5% to about 5% of a polyethylene wax; and
 (e) from about 1% to about 8% of hydrophobic organic esters (such as esters containing from about 10 to about 40 carbon atoms, for example cetearyl ethylhexanoate).

The compositions may optionally include from about 0.5% to about 5% of a suspending agent, such as a clay plus activator combination.

All percentages and ratios given herein are "by weight" unless otherwise specified.

All patents and publications referred to in this application are incorporated herein by reference, unless otherwise specified.

DETAILED DESCRIPTION OF THE INVENTION

The antiperspirant liquid compositions of the present invention include an antiperspirant active, a volatile solvent, a high molecular weight silicone material, a polyethylene wax, and hydrophobic organic esters, and may optionally contain additional components conventionally found in topical liquid-form antiperspirant compositions. Each of those components, as well as the methods of making and using the compositions of the present invention, will be discussed in detail below.

As used herein, the term "antiperspirant liquid" is intended to encompass all flowable compositions having a viscosity of from about 1,500 cps or less.

The present composition contains from about 10% to about 70%, preferably from about 15% to about 35%, by weight of an antiperspirant active material, generally in particulate form. These weight percentages are calculated on an anhydrous metal salt basis (exclusive of glycine, the salts of glycine, or other complexing agents). The antiperspirant material preferably has a particle size ranging about 1 to about 100 microns, more preferably from about 1 to about 50 microns. They may be impalpable or microspherical in form and, preferably, have a high bulk density (for example, greater than about 0.7 g/cm³). Any antiperspirant materials known in the art may be used in the compositions of the present invention. Such materials include, for example, many aluminum or zirconium astringent salts or complexes and are well-known in the antiperspirant art. Examples of useful antiperspirant materials are described in U.S. Pat. No. 6,287,544, Franklin, et al., issued Sep. 11, 2001; U.S. Pat. No. 6,261,543, Fletcher, et al., issued Jul. 17, 2001; and U.S. Pat. No. 6,187,301, Scavone, et al., issued Feb. 13, 2001; all incorporated herein by reference.

Aluminum salts of this type include aluminum chloride and the aluminum hydroxyhalides having the general formula $Al_2(OH)_xQ_y \cdot XH_2O$ where Q is chlorine, bromine or iodine; where x is from about 2 to about 5, x+y=about 6, and x and y do not need to be integers; and where X is from about 1 to about 6. Aluminum salts of this type can be prepared in the manner described more fully in U.S. Pat. No. 3,887,692, Gilman, issued Jun. 3, 1975, and U.S. Pat. No. 3,904,741, Jones and Rubino, issued Sep. 9, 1975, both incorporated herein by reference.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2-nz is greater than or equal to 0, and B may be selected from the group consisting of halides, nitrate, sulfamate, sulfate, and mixtures thereof. Although only zirconium compounds are exemplified in this context, it will be understood that other Group IV B metal compounds, including hafnium, could be used in the antiperspirant active component of the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than 0 groups per molecule.

Several types of antiperspirant complexes utilizing the above antiperspirant salts are known in the art. For example, U.S. Pat. No. 3,792,068, Luedders et al., issued Feb. 12, 1974, incorporated herein by reference, discloses complexes of aluminum, zirconium and amino acids such as glycines. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by:
 (A) co-dissolving in water
  (1) one part $Al_2(OH)_{6-m}Q_m$, wherein Q is an anion selected from the group consisting of chloride, bromide and iodide, and m is a number from about 0.8 to about 2.0;
  (2) x parts $ZrO(OH)_{2-a}Q_a \cdot nH_2O$, where Q is chloride, bromide or iodide; where a is from about 1 to about 2; where n is from about 1 to about 8, and where x has a value of from about 0.16 to about 1.2;
  (3) p parts neutral amino acid selected from the group consisting of glycine, dl-tryptophane, dl-β-phenylalanine, dl-valine, dl-methionine and β-alanine, and where p has a value of from about 0.06 to about 0.53;

(B) co-drying the resultant mixture to a friable solid; and
(C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl.2H_2O$. Preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2.nH_2O$ wherein a is from about 1.5 to about 1.87, and n is from about 1 to about 7. The preferred amino acid for preparing such ZAG-type complexes is glycine of the formula $CH_2(HN_2)COOH$. Salts of such amino acids can also be employed in the antiperspirant complexes. See U.S. Pat. No. 4,017,599, Rubino, issued Apr. 12, 1977, incorporated herein by reference.

A wide variety of other types of antiperspirant complexes are also known in the art. For example, U.S. Pat. No. 3,903,258, Siegal, issued Sep. 2, 1975, discloses a zirconium aluminum complex prepared by reacting zirconyl chloride with aluminum hydroxide and aluminum chlorhydroxide. U.S. Pat. No. 3,979,510, Rubino, issued Sep. 7, 1976, discloses an antiperspirant complex formed from certain aluminum compounds, certain zirconium compounds, and certain complex aluminum buffers. U.S. Pat. No. 3,981,896, issued Sep. 21, 1976, discloses an antiperspirant complex prepared from an aluminum polyol compound, a zirconium compound and an organic buffer. U.S. Pat. No. 3,970,748, Mecca, issued Jul. 20, 1976, discloses an aluminum chlorhydroxy glycinate complex of the approximate general formula

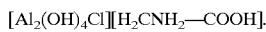

All of these patents are incorporated herein by reference.

Of all the above types of antiperspirant actives, preferred compounds include the 5/6 basic aluminum salts of the empirical formula $Al_2(OH)_5Cl.2H_2O$; mixtures of $AlCl_3.6H_2O$ and $Al_2(OH)_5Cl.2H_2O$ with aluminum chloride to aluminum hydroxychloride weight ratios of up to about 0.5; ZAG-type complexes wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5\ Cl.2H_2O$ wherein the total metal to chloride molar ratio in the complex is less than about 1.25, the Al:Zr molar ratio is about 3.3, and the amino acid is glycine; and ZAG-type complexes wherein the zirconium salt is $ZrO(OH)_{2-a}\ Cl_a.nH_2O$ wherein a is from about 1.5 to about 1.87 and n is from about 1 to about 7, the aluminum salt is $Al_2(OH)_5\ Cl.2H_2O$, and the amino acid is glycine.

Preferred particulate antiperspirant materials include inorganic or organic salts of aluminum, zirconium or zinc, as well as mixtures of those materials. Aluminum chlorhydrate (ACH) actives and aluminum zirconium tetrachlorohydrex glycine complex are particularly preferred antiperspirant actives for use in the present invention, with the aluminum zirconium tetrachlorohydrex glycine complex being particularly preferred.

The compositions of the present invention also include from about 20% to about 80%, preferably about 40% to about 60% of a volatile carrier. Such carriers generally include volatile hydrocarbon solvents, and volatile silicone solvents both of which are well-known for use in cosmetic and deodorant stick compositions. Volatile hydrocarbons, such as hydrocarbons including from about 10 to about 30 carbon atoms, that have sufficient volatility to slowly volatilize from the skin or hair after application of the topically effective composition can be used in the present invention.

The volatile hydrocarbons provide essentially the same functions and benefits as the volatile silicones described below, such as lubrication and a rich feel during application. The preferred volatile compound is an aliphatic hydrocarbon including from 12 to 14 carbon atoms, and having a boiling point in the range of from 100° C. to 300° C. Examples of volatile hydrocarbons useful in the compositions of the present invention are the commercially-available compounds Permethyl 99A and Permethyl 101A, available from Permethyl Corporation, Frazer, Pa. A volatile hydrocarbon compound is useful in the compositions of the present invention either alone, in combination with another volatile hydrocarbon, or in combination with a volatile silicone. The Permethyl compounds described above are those having the following formula, wherein n is 2 or 3:

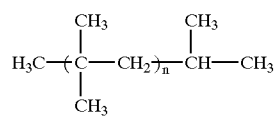

The volatile silicone materials used in the present invention are preferably either cyclic or linear polydimethylsiloxanes. The cyclic polydimethylsiloxanes preferably include from about 3 to about 7 silicon atoms, more preferably from about 4 to about 5 silicon atoms. The general formula for such siloxanes is

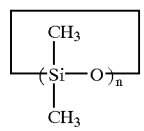

wherein n is from about 3 to about 7. The linear polydimethylsiloxanes contains from about 3 to about 9 silicon atoms and have the general formula,

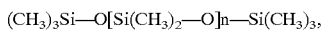

wherein n is from about 1 to about 7.

Silicones of the above type are commercially available, for example, from Dow Corning Corporation (Dow Corning 344, 345 and 200 fluids), General Electric Specialty Chemicals (SF 1202), and Stauffer Chemical (SWS-03314), as well as from Shin Etsu Chemicals.

The linear volatile silicone materials generally have viscosities of less than about 5 centistokes at 25° C. while the cyclic materials have viscosities less than about 10 centistokes. "Volatile," as used herein, means that the material has a measurable vapor pressure. A description of volatile silicones is found in Todd and Byers, "Volatile Silicone Fluids for Cosmetics", Cosmetics and Toiletries, 91:27–32 (1976), incorporated herein by reference.

Cyclic polydimethylsiloxanes, and particularly dimethicone D-5 (decamethylcyclopentasiloxane), and D-7 (tetradecamethylcycloheptasiloxane), are preferred for use in the compositions of the present invention.

The compositions of the present invention also contain from about 0.5% to about 5%, preferably from about 0.5% to about 2%, of a high molecular weight silicone material. This material should be non-polar and should have a molecular weight of at least about 5,000. Examples of such materials are well known in the art and include, for example, dimethicone polyether, crosslinked silicone elastomers, and silicone gums.

Polydiorganosiloxane-polyoxyalkylene copolymers (dimethicone polyols), are well known in the cosmetics and personal care arts and are described, for example, in U.S. Pat. No. 4,265,878, incorporated herein by reference, which further describes the copolymers and their methods of preparation. Briefly, polydiorganosiloxane-polyoxyalkylene copolymers are characterized by at least one polydiorganosiloxane segment and at least one polyoxyalkylene segment. The polydiorganosiloxane segment consists essentially of $R_nSiO_{(4-n)}$ units wherein n has a value of from 0 to 3 inclusive. There is an average of approximately two R radicals per siloxane unit in the copolymer with each R denoting a radical selected from the group consisting of methyl, ethyl, vinyl, phenyl and a divalent radical bonding the polyoxyalkylene segment to the polydiorganosiloxane segment. Useful polyoxyalkylene segments have an average molecular weight of from about 1000 to about 5000 and consist of from 0 to about 60 mole % polyoxypropylene units and from about 40 to about 100 mole % polyoxyethylene units. Polyoxyalkylene segments consisting of from about 40 to about 60 mole % of polyoxypropylene units and from about 40 to about 60 mole % of polyoxyethylene units are more preferred with segments consisting of an equimolar mixture of polyoxypropylene and polyoxyethylene units being most preferred. A terminal portion of each polyoxyalkylene segment is bonded to the polydiorganosiloxane segment.

For example, a preferred copolymer, with a weight ratio of about 2.8 polydiorganosiloxane segments to polyoxyalkylene segments, is characterized by the average formula:

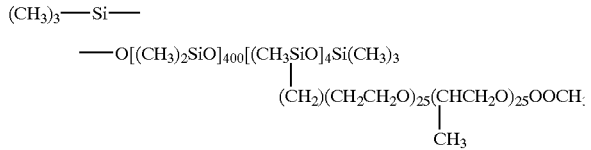

The crosslinked siloxane elastomers are also well-known in the cosmetic formulational arts. They are disclosed, for example, in U.S. Pat. No. 5,942,215, Edwards et al., issued Aug. 24, 1999, incorporated herein by reference. Siloxane elastomers are crosslinked or partially crosslinked, entangled, viscoelastic polymer networks, preferably made by the platinum catalyzed reaction known as hydrosilation of vinyl silicone fluids by either hydrosiloxane fluids or highly branched MQ hydride fluids. Control of the stoichiometry and type of the vinyl silicone fluid and the silanic crosslinker controls the properties of the cured networks. Additional vinyl reactants, such as vinyl alkenes can be introduced in the reactive medium to further modify the silicone network. The choice of the reaction solvent is also a means to modify the properties of the resultant materials. The average molecular weight of the silicone elastomers is between about 10,000 and about 40 million, and is preferably between about 10,000 and about 20 million. Typically, the crosslinked siloxane polymeric networks are swollen substantially by oily materials, preferably silicone fluids such as cyclomethicone and/or dimethicone.

Preferred crosslinked silicone materials are described in U.S. Pat. No. 5,654,362, Schulz, Jr., et al., issued Aug. 5, 1997, incorporated herein by reference. An example of such a material is Dow Coming 9040, commercially available from Dow Coming Corporation, Midland, Mich.

The liquid antiperspirant compositions of the present invention also include polyethylene materials and hydrophobic organic esters as formulation aids. The polyethylenes are generally present at from about 0.5% to about 5% of the composition. Polyethylene materials are known in the art as thickeners or skin feel improvers. They are generally available in the form of finely divided powders, for example under the trade name Accumist B6, commercially available from Honeywell, or Performalene 400 polymer, commercially available from New Phase Technologies.

The polyethylene material can be defined as a polyethylene wax having a melting point of greater than about 80° C. The polyethylene wax or waxes have the function of conferring on the product its necessary properties of spreading, of wear and of slip.

The polyethylene wax with a high melting point (>80° C.) used according to the invention is an ethylene homopolymer or a copolymer of ethylene and of another copolymerizable monomer corresponding to the following formula:

$$CH_2=CHR$$

in which R represents a linear or branched alkyl chain which can be interrupted by mono- or polyoxyalkylene units, an aryl or aralkyl radical or —$CH_2$ COOH or —$CH_2CH_2OH$ radical. The alkyl radicals more preferably denote the methyl, ethyl, propyl, isopropyl, decyl, dodecyl and octadecyl radicals. The mono- or polyoxyalkylene units preferably denote mono-or polypxyethylene groups. The aryl radical is preferably a phenyl or tolyl radical. The aralkyl radical is, for example, a benzyl or phenethyl radical.

The weight-average molar mass of the polyethylene wax is preferably between approximately 400 and 1000, more particularly between approximately 400 and 700, and is preferably about 500.

According to the preferred embodiment of the compositions according to the invention, the wax as defined above is chosen from ethylene homopolymers, copolymers of ethylene and of propylene, copolymers of ethylene and of maleic anhydride or acid, or oxidized or ethoxylated polyethylenes.

Mention may in particular be made, among the ethylene homopolymers which can be used according to the invention, of those sold under the names of Polywax 500, Polywax 655 and Polywax 1000 by Petrolite.

Mention may be made, among the ethylene copolymers which can be used according to the invention, of the copolymers of ethylene and of propylene sold under the names Ceramer® by Petrolite, the copolymers of ethylene and of maleic anhydride sold under the names Ceramer® by Petrolite, the oxidized polyethylenes sold under the names Unilin® and Unicid® by Petrolite, and the ethoxylated polyethylenes sold under the names Unithox® by Petrolite.

According to a particularly preferred embodiment of the invention, the polyethylene wax is an ethylene homopolymer wax.

The composition also includes a hydrophobic organic ester as a formulation aid (generally from about 1% to about 8% of the composition). Although the identity of the specific ester or combination of esters is not especially critical, it has been found that suitable esters include at least about 10 carbon atoms, and preferably the ester includes from about 10 to about 40 carbon atoms. For example, suitable esters encompass those comprising an alcohol or polyol including from 8 to about 20 carbon atoms and a carboxylic acid including from about 2 to about 12 carbon atoms, or conversely an alcohol or polyol including from 2 to about 12 carbon atoms with a carboxylic acid including from about 8 to about 20 carbon atoms. Examples of suitable esters include, but are not limited to, cetearyl ethylhexanoate (cetearyl octanoate), commercially available as Crodamol CAP, from Croda Chemical Company.

Esters are the covalent compounds formed between acids and alcohols. Esters can be formed from almost all acids (carboxylic and inorganic) and any alcohol. Esters used herein are derived from carboxylic acids and an alcohol. The general structure of these compounds is $R^4CO-OR^5$. The chain length for $R^4$ and $R^5$ generally can vary from 7 to 30 and can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, neopentyl glycol dioctanoate, dipropylene glycol dibenzoate, $C_{2-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol isoceteth-3 acetate, propylene glycol ceteth-3 acetate, octyldodecyl myristate, cetyl ricinoleate, myristyl myristate.

Preferred formulation aids are mixtures of the polyethylene and the organic ester components, such as mixtures of polyethylene and cetearyl ethylhexanoate. A preferred antiperspirant liquid composition contains from about 0.5% to about 2% (preferably about 1%) polyethylene and from about 2% to about 4% (preferably about 3%) cetearyl ethylhexanoate.

The liquid antiperspirant compositions of the present invention optionally contain a suspending agent. When such a suspending agent is used, it is generally present at from about 0.5% to about 5% of the composition. Suspending agents conventionally used in liquid topical products may be used in the compositions of the present invention. Examples of suspending agents which may be used in the present invention are disclosed in PCT Published Patent Application WO 00/69402, The Procter & Gamble Company, published Nov. 23, 2000, incorporated herein by reference. The term "suspending agent," as used herein, defines any material known or otherwise effective in providing suspending, gelling, viscosifying, solidifying, or thickening properties to the liquid composition or which otherwise would provide structure to the final product form. Such materials can be used to suspend the components in antiperspirant compositions of the present invention, as well as to provide additional viscosity for the roll-on product. Suitable suspending agents for use in the present compositions include, but are not limited to, fatty acid gellants, salts of fatty acids, hydroxy acid gellants, esters and amides of fatty acid or hydroxy fatty acid gellants, cholestcrolic materials, dibenzylidenc alditols, lanolinolic materials, fatty alcohols, triglycerides, sucrose esters, inorganic materials, such as clays or silicas, and other suitable gellants.

A preferred suspending agent for use in the present invention is a clay material, such as a quaternium-18 hectorite material (Bentone 38 VCG, commercially available from NL Industries, Inc. (formerly National Lead Company) and is described in greater detail in the Technical Bulletin from the National Lead Company entitled "BENTONE 38" (incorporated by reference), together with an activator material such as propylene carbonate or ethanol.

Nonlimiting examples of such other optional materials include dyes or colorants, emulsifiers, perfumes, distributing agents, pharmaceutical or other topical actives, preservatives, surfactants, processing aids such as viscosity modifiers, wash-off aids, and so forth. These materials are used at their conventional usage levels to provide their conventional benefits. Examples of such optional materials are described in U.S. Pat. No. 4,049,792, Elsnau; U.S. Pat. No. 5,019,375, Tanner, et al.; and U.S. Pat. No. 5,429,816, Hofrichter, et al.; all of which are incorporated herein by reference.

The compositions of the present invention may be manufactured using methods known in the art. Typically, the following steps may be followed:

Step A) The suspending agent and activator are added to the volatile carrier. The mixture is heated to about 60° C.+/−5° C. and homo-mixed using an IKA-Wereke Ultra Turrax T50 at a fixed speed of about 5000 rpm.

Step B) The mixture is mixed and homo-mixed at the same rate and temperature for at least 15 minutes, during which time the suspending agent becomes hydrated and the mixture becomes viscous.

Step C) In a separate mixing vessel, the emollient is mixed and heated to a temperature of about 80° C.+/−5° C. Once that temperature is achieved, the polyethylene material is added.

Step D) After the polyethylene material is melted, the temperature of the mixture is reduced to about 60° C.+/−5° C. This mixture is then added to the volatile carrier mixture while maintaining the 60° C.+/−5° C. temperature.

Step E) All other materials are added to this mixture while maintaining the 60° C.+/−5° C. temperature. The mixture is mixed and homo-mixed at the same rate at the 60° C.+/−5° C. temperature for at least 50 minutes.

Step F) The mixture is cooled to a temperature of about 50° C.+/−5° C. while continuing to mix and homo-mix. Mixture is poured into commercially available roll-on packages.

The low residue antiperspirant liquid roll-on compositions of the present invention are used in a conventional manner. Specifically, the compositions may be used to prevent and/or control perspiration wetness by topically applying, one or more times a day, an effective amount of the composition to areas of the body particularly prone to perspiration (for example, the underarm area).

The following nonlimiting examples illustrate the compositions, methods of making, and methods of using the present invention described in the present application.

EXAMPLES

Antiperspirant liquid roll-on compositions of the present invention, having the compositions given in the table below, are formulated using the procedures described above. The compositions are stable, and provide good antiperspirant performance with good skin feel and minimized skin whitening.

| Ingredient Name | Example 1 | Example 2 | Example 3 | Example 4 | Example 5 |
| --- | --- | --- | --- | --- | --- |
| Cyclomethicone | 47.00 | 49.75 | 52.00 | 52.00 | 52.00 |
| Quaternium 18 Hectorite | 5.00 | 5.00 | 3.00 | 3.00 | 3.00 |
| Propylene Carbonate | 1.00 | 1.00 | | | 0.75 |
| Ethanol | | | 1.00 | 1.00 | |
| Dipropylene Glycol | | | 1.00 | 1.00 | 1.00 |
| PPG-3 Myristyl Ether | 2.00 | 2.00 | | | |
| Polyethylene | 3.00 | 3.00 | 2.00 | 2.00 | 1.00 |
| Petrolatum | 4.75 | 2.25 | 4.50 | 5.00 | 9.25 |
| Mineral Oil | 10.00 | 10.00 | 8.00 | 8.00 | 6.00 |
| Dimethicone Copolyol | 0.75 | 1.00 | | | |
| Silicone Elastomer | 1.00 | 0.50 | 2.00 | 2.00 | 1.00 |
| Cetearyl Ethylhexanoate | 1.00 | 1.00 | 2.00 | 1.50 | 1.50 |
| Al Zr Tetrachlorohydrex | 24.00 | 24.00 | 24.00 | 24.00 | 24.00 |

-continued

| Ingredient Name | Example 1 | Example 2 | Example 3 | Example 4 | Example 5 |
|---|---|---|---|---|---|
| Glycinate | | | | | |
| Fragrance | 0.50 | 0.50 | 0.50 | 0.50 | 0.50 |

What is claimed is:

1. A liquid antiperspirant composition comprising:
   (a) from about 10% to about 70% of an antiperspirant active;
   (b) from about 20% to about 80% of a volatile carrier;
   (c) from about 0.5% to about 5% of a high molecular weight silicone material;
   (d) from about 0.5% to about 5% of a polyethylene wax; and
   (e) from about 1% to about 8% of hydrophobic organic esters.

2. The antiperspirant composition according to claim 1 wherein the volatile carrier is a volatile silicone material.

3. The antiperspirant composition according to claim 2 wherein the high molecular weight silicone is selected from silicone gums, crosslinked silicone polymers, dimethicone polyether, and mixtures thereof.

4. The antiperspirant composition according to claim 3 wherein the hydrophobic organic ester material contains from about 10 to about 40 carbon atoms.

5. The antiperspirant composition according to claim 4 wherein the volatile solvent is selected from cyclic polydimethylsiloxanes containing from about 3 to about 7 silicon atoms, linear polydimethylsiloxanes containing from about 3 to about 9 silicon atoms, and mixtures of thereof.

6. The antiperspirant composition according to claim 5 wherein the antiperspirant active comprises materials selected from organic or inorganic salts of aluminum, zirconium, zinc, and mixtures thereof.

7. The antiperspirant composition according to claim 6 which contains from about 15% to about 35% of the antiperspirant active, and from about 40% to about 60% of the volatile carrier.

8. The antiperspirant composition according to claim 7 which contains from about 0.5% to about 2% of the polyethylene component and from about 2% to about 4% of the hydrophobic organic ester component.

9. The antiperspirant composition according to claim 8 wherein the volatile silicone carrier is selected from decamethylcyclopentasiloxane, tetradecamethylcycloheptasiloxane, and mixtures thereof.

10. The antiperspirant composition according to claim 5 wherein the formulation aid is a mixture of polyethylene and cetearyl ethylhexanoate.

11. The antiperspirant composition according to claim 10 which comprises from about 0.5% to about 2% polyethylene and from about 2% to about 4% cetearyl ethylhexanoate.

12. The antiperspirant composition according to claim 1 which additionally comprises from about 0.5% to about 5% of a suspending agent.

13. The antiperspirant composition according to claim 12 wherein the suspending agent is a clay material together with an activator.

14. The antiperspirant composition according to claim 9 which additionally comprises from about 0.5% to about 5% of a suspending agent.

15. The antiperspirant composition according to claim 11 which additionally comprises from about 0.5% to about 5% of a suspending agent.

* * * * *